United States Patent
Grand-Clement et al.

(10) Patent No.: US 11,944,381 B2
(45) Date of Patent: Apr. 2, 2024

(54) PROCESS OF CORRECTION OF THE SHIFT DUE TO TEMPERATURE OF THE OPTICAL POWER OF AN ACTIVE LENS OF A PHOROPTER AND RELATED PHOROPTER AND OPTOMETRY SYSTEM

(71) Applicant: Essilor International, Charenton-le-Pont (FR)

(72) Inventors: Didier Grand-Clement, Charenton-le-Pont (FR); Philippe Pinault, Charenton-le-Pont (FR); Yones Sidiq de Labrusse, Toulouse (FR)

(73) Assignee: Essilor International, Charenton-le-Pont (FR)

( * ) Notice: Subject to any disclaimer, the term of this patent is extended or adjusted under 35 U.S.C. 154(b) by 316 days.

(21) Appl. No.: 17/295,363

(22) PCT Filed: Nov. 20, 2018

(86) PCT No.: PCT/IB2018/001446
§ 371 (c)(1),
(2) Date: May 19, 2021

(87) PCT Pub. No.: WO2020/104826
PCT Pub. Date: May 28, 2020

(65) Prior Publication Data
US 2022/0015623 A1 Jan. 20, 2022

(51) Int. Cl.
*A61B 3/028* (2006.01)
*A61B 3/00* (2006.01)
(Continued)

(52) U.S. Cl.
CPC .......... *A61B 3/0285* (2013.01); *A61B 3/0016* (2013.01); *G02B 3/14* (2013.01); *G02B 7/028* (2013.01)

(58) Field of Classification Search
CPC .......... A61B 3/0285; G02B 3/12; G02B 3/14
(Continued)

(56) References Cited

U.S. PATENT DOCUMENTS 7,413,306 B2 * 8/2008 Campbell ............ G02B 26/004
359/666
11,181,670 B2 * 11/2021 Song ........................ G02B 3/14
(Continued)

FOREIGN PATENT DOCUMENTS

EP    1 411 382 A2    4/2004
EP    2 860 555 A1    4/2015
(Continued)

OTHER PUBLICATIONS

International Search Report dated Jul. 18, 2019 in PCT/IB2018/001446 filed Nov. 20, 2018.

*Primary Examiner* — Zachary W Wilkes
(74) *Attorney, Agent, or Firm* — Oblon, McClelland, Maier & Neustadt, L.L.P.

(57) ABSTRACT

A process, phoropter, and an optometry system, the process being for correction of the shift of the optical power of an active lens in a phoropter due to a temperature change over time, the active lens including a container filled with a liquid and having a deformable curvature membrane under the action of an actuator controlled by an optical power control command, the shift being that the active lens provides an actual optical power that is different from the expected optical power corresponding to the optical power control command. A temperature sensor is arranged in and/or on the phoropter to measure the temperature in the phoropter.

10 Claims, 1 Drawing Sheet

(51) Int. Cl.
  *G02B 3/14*   (2006.01)
  *G02B 7/02*   (2021.01)
(58) Field of Classification Search
  USPC .................................................. 359/665–666
  See application file for complete search history.

(56) References Cited

U.S. PATENT DOCUMENTS

| | | | |
|---|---|---|---|
| 11,194,221 B2* | 12/2021 | Jang .......................... | G02B 7/09 |
| 11,209,576 B2* | 12/2021 | Patscheider .............. | G02B 3/14 |
| 2014/0307252 A1 | 10/2014 | Hinderling et al. | |
| 2018/0136372 A1* | 5/2018 | Patscheider .............. | G02B 3/14 |
| 2021/0231907 A1* | 7/2021 | Park .......................... | G02B 3/14 |

FOREIGN PATENT DOCUMENTS

| | | |
|---|---|---|
| EP | 2 869 097 A1 | 5/2015 |
| WO | WO 2016/203029 A1 | 12/2016 |

* cited by examiner

PROCESS OF CORRECTION OF THE SHIFT DUE TO TEMPERATURE OF THE OPTICAL POWER OF AN ACTIVE LENS OF A PHOROPTER AND RELATED PHOROPTER AND OPTOMETRY SYSTEM

TECHNICAL FIELD OF THE INVENTION

The invention relates to the domain of refractive active lenses in optical systems and more particularly the use of such lenses in optometry.

More precisely the invention relates to a process of correction of the shift of the optical power of an active lens, such as a deformable liquid lens, used in a phoropter for subjective measurement of refraction, said shift being due to temperature variations in the phoropter. The invention also relates to a phoropter with an active lens and adapted to execute the process and to an optometry system.

BACKGROUND INFORMATION AND PRIOR ART

Phoropter that should be able to provide lens with different optical power are known. Usually, a set of lenses having different optical powers is arranged in the phoropter with the possibility of selecting the one of the requested optical power. This involves complicated mechanical systems and it has been proposed to use a tunable optical system that is an active lens which optical power can be changed under the control of an optical power control command, that is practically an electric signal.

An active lens of the liquid lens type is known for example from the company Optotune AG, wherein said active lens has a variable optical power under the control of such an optical power control command.

The optical power of such an active lens is changed according to the deformation of a deformable membrane, e.g. an elastic polymer membrane, under the action of an actuator, a circular ring, that pulls/pushes onto the center of the membrane so as to modify its shape (concave or convex), in particular its radius of curvature, the circular ring receiving the optical power control command.

The variable optical power of the lens then depends on the shape of the membrane, and on the optical properties (e.g. indices of refraction) of the transparent fluid filling the active lens.

Hence, depending on the temperature acting on the different parts of the active lens and notably its internal liquid and its mounting elements including the circular ring, the optical power may be modified with respect to its nominal value that is defined for a typical temperature of utilisation. At the typical temperature of utilisation, the actual (the real one that can be measured) optical power of the active lens is equal to the expected optical power corresponding to the optical power control command that is sent to the active lens. Indeed, a response curve giving the optical power control command to send to the active lens as a function of the expected optical power with the active lens at the typical temperature of utilisation, is generally available and at that temperature the actual optical powers are equal to the expected ones. When the active lens is no more at the typical temperature of utilisation, the actual optical power of the active lens is no more equal to the expected one.

SUMMARY OF THE INVENTION

Therefore, one object of the invention is to provide a process to correct the shift of the optical power of the active lens that is due to temperature variations within the phoropter.

The above object is achieved according to the invention by a process of correction of the shift of the optical power of an active lens in a phoropter due to a temperature change over time, the active lens comprising a container filled with a transparent liquid and having a deformable curvature membrane under the action of an actuator controlled by an optical power control command, the shift being that the active lens provides an actual optical power that is different from the expected optical power corresponding to the optical power control command, wherein a temperature sensor is arranged in the phoropter to measure the temperature in the phoropter, wherein in a preliminary phase, a static curve or function of the actual optical power of at least one determined active lens as a function of measured temperatures is obtained for at least one constant value of optical power control command and in a steady state condition, wherein in a further utilization phase of the phoropter, the current temperature is measured by the temperature sensor and the active lens receives an optical power control command that is corrected using the static curve or function of the actual optical power of the active lens to bring back the actual optical power equal to the expected optical power.

The following characteristics that can be used alone or according to any technical combination are also considered in the context of the process of the invention:

the steady state condition is when the at least one determined active lens has reached a stable temperature after a change of temperature and for which the optical power of the said at least one determined active lens does not change anymore, i.e. the shift is constant/stable, in the preliminary phase, the at least one determined active lens is subjected to different temperatures and for each temperature used to measure the optical power, the at least one determined active lens is in a steady state condition when the optical power is measured, in the further utilization phase of the phoropter, the static correction is done when the at least one determined active lens is in a steady state condition, in the preliminary phase, the measured temperature is measured by the temperature sensor of the phoropter, in the preliminary phase, the measured temperature is measured by an independent temperature sensor of the phoropter, in the preliminary phase, the static curve or function of the actual optical power is obtained with the active lens(es) in the phoropter(s), in the preliminary phase, the static curve or function of the actual optical power is obtained with the active lens(es) not yet in the phoropter(s), in the preliminary phase, the at least one determined active lens is the active lens of the phoropter that will be used in the further utilization phase and the temperature is measured with the temperature sensor of the phoropter in the preliminary phase, in the preliminary phase, the at least one determined active lens are the active lenses of a batch of phoropters that are due to be used in further utilization phases and the temperatures are measured with the temperature sensors of the phoropters of the batch in the preliminary phase and wherein the static curve or function of the actual optical power is the result of the statistical combination of the obtained static curves or functions of each phoropter of the batch, the statistical combination being selected from an average, a median value, in the preliminary phase, the at least one determined active lens is the active lens of the phoropter that will be used in the further utilization phase and the static curve or function of the actual optical power of the active lens is provided by the manufacturer of the active lens, in the preliminary phase, a static curve or function of the actual optical power of the active lens as a function of measured temperatures for at least one constant value of optical power control command and in a steady state condition where the phoropter is subjected to different temperatures and for each temperature used to measure the optical power, the active lens has reached a stable optical power, during the preliminary phase, the correction of the optical power control command is inoperative or set to zero, each expected optical power corresponds to a given optical power control command different from the others and that is supposed (because it is not possible to exclude a possible ageing of the components of the phoropters . . . ) to be constant over time, as a consequence the relation between values of expected optical power and of optical power control command is perfectly defined and it is possible to know the value of one of them knowing the value of the other, in further utilization phase of the phoropter, the temperature sensor assesses the evolution of the temperature and when the evolution of the temperature is so slow to allow the active lens to be in a steady state or quasi steady state as regard the evolution of the temperature, the correction is fully done, in further utilization phase of the phoropter, the temperature sensor assesses the evolution of the temperature and when the evolution of the temperature is not so slow to allow the active lens to be in a steady state or quasi steady state as regard the evolution of the temperature, each correction is progressively done over time, during the preliminary phase, for obtaining the static curve or function of the actual optical power of the active lens as a function of the temperature, the phoropter is subjected to different external temperatures that are provided by a thermal chamber, the phoropter being installed in said thermal chamber, during the preliminary phase, for obtaining the static curve or function of the actual optical power of the active lens as a function of the temperature, the phoropter is subjected to different internal temperatures that are provided by at least one internal or integral thermal source within the phoropter, preferably the phoropter being in a thermally stable environment, the phoropter can be switched on or off and comprises electronic and electric and, possibly, mobile mechanical parts, that warm up when the phoropter is switched on, and thus forming internal or integral thermal sources, for obtaining the static curve or function of the actual optical power of the active lens as a function of the temperature, the preliminary phase is done with, at the beginning, the phoropter switched off since a sufficient time to be in a steady state as regard temperature, for obtaining the static curve or function of the actual optical power of the active lens as a function of the temperature, the preliminary phase is done with, at the beginning, the phoropter switched on since a sufficient time to be in a warmed up steady state as regard temperature, the static curve or function of the actual optical power of the active lens as a function of the temperature is obtained with different temperatures within a range of temperatures, the range of temperatures is continuous between a min and a max temperature, the range of temperatures is discrete between a min and a max temperature, the min ambient temperature of the range of temperatures is about 10° C., the max ambient temperature of the range of temperatures is about 40° C., the phoropter is tropicalized and the range of temperatures is 16° C. to 28° C., the static curve or function of the actual optical power of the active lens as a function of the temperature is obtained with a slow variation of the temperature to allow the active lens to be in a steady state or quasi steady state as regard the variation of the temperature and the actual optical power is measured continuously or discretely, the static curve or function of the actual optical power of the active lens as a function of the temperature is obtained with variations by steps of the temperature and the actual optical power is measured when the active lens is in a steady state as regard the temperature, the static curve or function of the actual optical power of the active lens as a function of the temperature is defined relatively to a reference temperature, in the preliminary phase, the static curve or function of the actual optical power of the active lens as a function of the temperature is expressed as a function defined relatively to a reference temperature Tref and to a related reference optical power Pref: Pcurrent=Pref+$\alpha$*(TCurrent−Tref) where Pcurrent is the actual optical power and $\alpha$ the sensitivity to the temperature, in the preliminary phase, a set of static curves or functions of the actual optical power of the active lens as a function of the temperature measured by the temperature sensor is obtained for a set of different constant values of optical power control command and in steady state condition, and wherein in the further utilization phase of the phoropter, for the correction, the active lens receives an optical power control command that is corrected using the static curve or function from the set of static curves of functions with the constant value of optical power control command that is equal or the closest to the optical power control command for the expected optical power, the temperature sensor is arranged in a device that has the same specific heat than the one of the active lens in order to have the temperature sensor having the same dynamic evolution of temperature as the active lens, in the preliminary phase, a further dynamic curve or function of the actual optical power of the active lens as a function of the time is obtained for at least one constant value of optical power control command and for at least one defined step of temperature change, the actual optical power becoming constant after a settle time as from the start of the step of temperature change, and wherein in the further utilization phase of the phoropter, the active lens receives an optical power control command that is further corrected using the dynamic curve or function of the actual optical power of the active lens to bring back the actual optical power equal to the expected optical power, in the preliminary phase, the dynamic curve or function of the actual optical power is obtained with the active lens(es) in the phoropter(s), in the preliminary phase, the dynamic curve or function of the actual optical power is obtained with the active lens(es) not yet in the phoropter(s), in the preliminary phase, the at least one determined active lens are the active lenses of a batch of phoropters that are due to be used in further utilization phases and the temperatures are measured with the temperature sensors of the phoropters of the batch in the preliminary phase and wherein the dynamic curve or function of the actual optical power is the result of the statistical combination of the obtained dynamic curves or functions of each phoropter of the batch, the statistical combination being selected from an average, a median value, in the preliminary phase, the at least one determined active lens is the active lens of the phoropter that will be used in the further utilization phase and the dynamic curve or function of the actual optical power of the active lens is provided by the manufacturer of the active lens, during the preliminary phase, for obtaining the dynamic curve or function of the actual optical power of the active lens as a function of the time, the phoropter is subjected to at least one defined step of temperature change that is provided by a thermal chamber, the phoropter being installed in said thermal chamber, during the preliminary phase, for obtaining the dynamic curve or function of the actual optical power of the active lens as a function of the time, the phoropter is subjected to at least one defined step of temperature change that is provided by at least one internal or integral thermal source within the phoropter, preferably the phoropter being in a thermally stable environment, the at least one internal or integral thermal source of the phoropter comprises electronic and electric and, possibly, mobile mechanical parts, that warm up when the phoropter is switched on, the at least one internal or integral thermal source of the phoropter further comprises a controlled heating resistor, for obtaining the further dynamic curve or function of the actual optical power of the active lens as a function of the time, the preliminary phase is done with, at the beginning, the phoropter switched off since a sufficient time to be in a steady state as regard temperature, for obtaining the further dynamic curve or function of the actual optical power of the active lens as a function of the time, the preliminary phase is done with, at the beginning, the phoropter switched on since a sufficient time to be in a warmed up steady state as regard temperature, the phoropter can be switched on or off and comprises electronic and electric and, possibly, mobile mechanical parts, that warm up when the phoropter is switched on, the phoropter can be switched on or off and comprises electronic and electric and, possibly, mobile mechanical parts, that warm up when the phoropter is switched on, and wherein during the preliminary phase for obtaining the further dynamic curve or function of the actual optical power of the active lens as a function of the time, the defined step of temperature change is only obtained by switching on or off the phoropter, the change of temperature step is defined by an initial temperature and a final temperature, the initial temperature is lower than the final temperature, the initial temperature is higher than the final temperature, the change of temperature step is defined by a speed of evolution of the temperature between the initial temperature and the final temperature, the speed of evolution of the change of temperature step is the highest possible, the speed of evolution of the change of temperature step is higher than the speed allowing the active lens to be in a steady state or quasi steady state as regard the evolution of the temperature, the phoropter can be switched on or off and comprises electronic and electric and, possibly, mobile mechanical parts, that warm up when the phoropter is switched on, and wherein during the preliminary phase for obtaining the further dynamic curve or function of the actual optical power of the active lens as a function of the time, the defined step of temperature change is only obtained by switching on the phoropter, when switching off or on the phoropter, the speed of evolution of the change of temperature step is higher than the speed allowing the active lens to be in a steady state or quasi steady state as regard the evolution of the temperature, in the further utilization phase of the phoropter, the active lens receives an optical power control command that is further corrected using the dynamic curve or function of the actual optical power of the active lens as a function of the time to bring back the actual optical power equal to the expected optical power, the value of the correction being dependent of the time since the switching on of the phoropter, in the further utilization phase of the phoropter, when the phoropter is switched on after having been in a steady state for the temperature and that the time since the switching on of the phoropter is greater as the settle time, no correction is done based on the dynamic curve or function of the actual optical power of the active lens, the active lens receives an optical power control command that is further corrected using the dynamic curve or function of the actual optical power of the active lens as a function of the time to bring back the actual optical power equal to the expected optical power, the value of the correction being dependent of the time since the moment the evolution of the temperature has a speed so high as to not allow the active lens to be in a steady state or quasi steady state as regard the evolution of the temperature, in the further utilization phase of the phoropter, the active lens receives an optical power control command that is further corrected using the dynamic curve or function of the actual optical power of the active lens as a function of the time to bring back the actual optical power equal to the expected optical power, the value of the correction being dependent of the initial temperature when the change of temperature started and of the current temperature measured by the temperature sensor of the phoropter, in the further utilization phase of the phoropter, the active lens receives an optical power control command that is further corrected using the dynamic curve or function of the actual optical power of the active lens as a function of the time to bring back the actual optical power equal to the expected optical power, the value of the correction being dependent of the initial temperature when the evolution of the temperature has a speed so high as to not allow the active lens to be in a steady state or quasi steady state as regard the evolution of the temperature, and of the current temperature measured by the temperature sensor of the phoropter, in the further utilization phase of the phoropter, one uses for the correction a global function corresponding to the combination of the static and dynamic curves or functions of the actual optical power of the active lens, in the further utilization phase of the phoropter, one uses for the correction a global function that is defined relatively to a reference temperature Tref and to a related reference optical power Pref: Pcurrent=Pref+α*(Tcurrent−Tref+β*e$^{-(t/\delta)}$) where Pcurrent is the actual optical power, α the sensitivity to the temperature, β a temperature coefficient, δ a coefficient related to the dynamic of the reactivity of the system, essentially related to the one of the liquid of the active lens, and t the time since the change of temperature occurred or started, in the further utilization phase of the phoropter, one uses for the correction a global function that is defined relatively to a reference temperature Tref and to a related reference optical power Pref: Pcurrent=Pref+α*(Tcurrent−Tref+γ*(TswitchOn−TlastSwitchOff)*e$^{-(t/\delta)}$)) where Pcurrent is the actual optical power, a the sensitivity to the temperature, γ a temperature coefficient, δ a coefficient related to the dynamic of the reactivity of the system, essentially related to the one of the liquid of the active lens, and TswitchOn the measured temperature when the phoropter was switched on and TlastSwitchOff the temperature when the phoropter was switched off for the last time, the correction is given by the difference between Pexpected−Pcurrent, in the preliminary phase, a set of dynamic curves or functions of the actual optical power of the active lens is obtained for a set of different constant values of optical power control command, and wherein in the further utilization phase of the phoropter, for the correction, the active lens receives an optical power control command that is corrected using the dynamic curve or function from the set of dynamic curves of functions with the constant value of optical power control command that is equal or the closest to the optical power control command for the expected optical power, in the preliminary phase, a set of dynamic curves or functions of the actual optical power of the active lens is obtained for a set of different initial temperature values, and wherein in the further utilization phase of the phoropter, for the correction, the active lens receives an optical power control command that is corrected using the dynamic curve or function from the set of dynamic curves of functions with the initial temperature value that is equal or the closest to the current temperature value at the beginning of the change of temperature, a computing system is arranged in the phoropter, said computing system generating and correcting the optical power control command, and the static and, if obtained, the dynamic curves or functions are stored in a memory of the computing system of the phoropter.

The invention also proposes a phoropter comprising at least one active lens. Typically, the phoropter comprises a pair of active lenses.

More precisely, it is proposed a phoropter comprising at least one active lens and a computing system, the active lens comprising a container filled with a transparent liquid and having a deformable curvature membrane under the action of an actuator controlled by an optical power control command, wherein the phoropter comprises means configured for the execution of the described process.

The invention also proposes a phoropter comprising at least one active lens, the active lens comprising a container filled with a transparent liquid and having a deformable curvature membrane under the action of an actuator controlled by an optical power control command, wherein the phoropter comprises a temperature sensor that is arranged in a device that has the same specific heat than the one of the active lens in order to have the temperature sensor having the same dynamic evolution of temperature as the active lens.

The invention also proposes a phoropter comprising at least one active lens, the active lens comprising a container filled with a transparent liquid and having a deformable curvature membrane under the action of an actuator controlled by an optical power control command, the active lens being susceptible to a shift of its optical power due to a temperature change, the shift being that the active lens provides an actual optical power that is different from the expected optical power corresponding to the optical power control command, said phoropter comprising two active lenses and two temperature sensors, each temperature sensor being arranged on its corresponding active lens, and wherein each active lens receives an optical power control command that is shift corrected based on the temperature measured by its own temperature sensor.

The invention is also directed to an optometry system comprising a phoropter and a computing system, the phoropter comprising at least one active lens, the active lens comprising a container filled with a liquid and having a deformable curvature membrane under the action of an actuator controlled by an optical power control command, said optometric system comprising means configured for the execution of the described process.

DETAILED DESCRIPTION OF EXAMPLE

The following description, enriched with joint drawings that should be taken as non-limitative examples, will help understand the invention and figure out how it can be realized.

For the following explanations and for simplicity reasons, a phoropter having one active lens will be considered but, generally, phoropters are used for examining the two eyes of a patient and two active lenses are used in each phoropter.

Note that the invention can be applied independently to each active lens of the phoropter in the sense that each active lens has a corresponding temperature sensor and correction means that are independent from the other active lens. But, the invention can also be applied in the phoropter with only one temperature sensor for a plurality of active lenses. In all cases, it is most preferable that each active lens of the phoropter has its own curve or function of actual optical power as a function of the measured temperatures (or set of curves or functions).

Alternatively, it may be possible to use only one (or a set) curve or function of the actual optical power as a function of the measured temperatures for all the active lenses of the phoropter but that has been statistically obtained from the actual actives lenses of the phoropter or a batch of active lenses used to make phoropters.

As we have seen in the introductory part, the optical power of the active lens evolves as its temperature changes. The causes of temperature changes may be numerous with external causes, for example change of the temperature of the room where the phoropter is installed, or internal causes due to internal parts, notably electric and electronic circuits that heat-up when the phoropter is switched-on and cool-down when switched-off.

In a phoropter having no mean to correct the shift of the optical power of the active lens due to temperature change or in which such a correcting mean is switched off, it is possible to measure the optical power of the active lens as a function of the temperature to which the active lens is subjected. For that purpose, a temperature sensor is arranged inside the phoropter with which the temperature is measured. Due to the fact that the transmission of the heat or cold is not instantaneous, there are some cases where the phoropter is not in a steady state as regards the temperature and some part of it, notably the active lens, may see its temperature still evolving while the measured temperature is stable and, as a consequence, the shift of optical power due to temperature will still evolve while the measured temperature is stable. The previous evolving shift characterises a dynamic behaviour of the phoropter as regards temperature. Of course, without temperature change for a sufficient long time, the phoropter will go in a steady state for temperature and the shift of optical power due to temperature will stay stable. The previous stable shift characterises a static behaviour of the phoropter as regards temperature and it refers to a steady state of the phoropter for temperature.

If the user of the phoropter has time to wait for the phoropter to go in a steady state, only the static shift due to static behaviour is to be considered for correcting the shift of optical power due to temperature. Thus, in a phoropter in a steady state for temperature, the temperature is measured and knowing the static behaviour of the phoropter that can be expressed with a curve or function of the optical power as a function of the temperature for a given constant optical power control command (or a constant expected optical power as this is equivalent), it is possible to correct the command sent to the active lens in order to have the actual optical power equal to the expected optical power. The static behaviour can be expressed as an optical power shift as a function of the temperature, or expressed relatively to a reference temperature that can, for example, be the typical temperature of utilisation.

Note that the static behaviour of the phoropter can be expressed with a plurality/a set of curves or functions, each one for a constant optical power control command (or a constant expected optical power as this is equivalent) or even expressed as a 3D representation or function of the optical power as a function of both the temperature and the optical power control command (or a constant expected optical power as this is equivalent). In that later case, for the correction, the level of the optical power control command or the expected optical power as this is equivalent, is also considered, for example one uses the curve made with the same or closest optical power control command or, equivalently, the expected optical power. The consideration of various levels of the optical power control command or equivalently the expected optical power, can also apply to the different ways of expressing the static behaviour such as an optical power shift as a function of the temperature, or relatively to a reference temperature.

However, this is generally not possible to wait for steady state because the time needed to go in a steady state for all parts of the phoropter may be quite long and/or it may be difficult to have a constant temperature in the environment of the phoropter. The dynamic behaviour of the phoropter should then be taken into account for correcting the shift. This can be done in many ways. For example, the dynamic behaviour may be always taken into account (the phoropter being or not in steady state for temperature) but the related correction (dynamic correction) being null or negligible when the phoropter goes into steady state, or, conversely, the dynamic behaviour is only taken into account when one detects that the phoropter leaves a steady state. Moreover, the notion of steady state can be referred to a constant temperature but also to a varying temperature but with a rate of change so low that there is always a balance/equality between the measured temperature by the temperature sensor and the temperature of the active lens. In the latter case, the static correction appears sufficient to correct the shift for such a slow change of temperature. Also, when the measured temperature is stabilized for a sufficient long time, the dynamic behaviour will finally correspond to the static one. It is important to note here that, in all cases, the static correction is always considered/executed (even if the level of correction is null because the measured temperature in the steady state is the typical temperature of utilisation).

For the assessment of the dynamic behaviour of the phoropter one can consider multiple parameters such as, for example, the instantaneous or not rate of change of temperature, the duration of change and the temperatures at the start and at the end (the end corresponding to the moment at which the correction is done), the start time and end time . . . .

In general, when used to examine the patients, the phoropters are in rooms in which the temperature does not change a lot and sharply and the cause of temperature change is most of the time internal to the phoropter and due to the switching on or off of the phoropter. Therefore, the switching times are elements that could be usefully considered in relation to the dynamic behaviour.

A practical example is now given that will show one of the multiple ways the static and dynamic behaviours of the phoropter can be assessed. The assessments of the static and possibly dynamic behaviours of the active lens(es) and, more generally of the phoropter, to get the static and possibly dynamic curves or functions of the actual optical power as a function of at least the temperature, are done in a preliminary phase, before the utilization phase of the phoropter. This preliminary phase can be considered as an initial calibration phase of the phoropter. As previously seen, this calibration can be done with the phoropter comprising its active lenses or directly on the active lenses, possibly a batch of them, before they are installed in the phoropter.

Preferably, such assessments are done on the integral phoropter but, in some cases, specifically for the static behaviour, it can be done directly on the active lens before it is installed in the phoropter.

The phoropter is positioned in a controlled temperature chamber and means to measure the actual optical power of the active lens are arranged on the phoropter and, preferably, in such an arrangement that do not interfere with heat exchanges of the phoropter.

For the static behaviour, measurements of the optical power of the active lens are done for multiple temperatures and when the phoropter is in a steady state for temperature, i.e. the temperature is stable for a sufficient long time that the optical power does not change any more. Of course, those measurements are done with all other controllable parameters that could modify the optical power constant and notably the optical power control command that is set to a defined value. As seen previously, this can be repeated for other values of the other controllable parameters and typically for other values of optical power control command. This last possibility is useful in case there are some non-linearities in the response of the active lens with different values of optical power control command with regards to the variation of the temperature.

With all those measurements, it is possible to create with known mathematical tools a static curve or a static function of the actual optical power of the active lens as a function of the temperature measured by the temperature sensor. For example, the static behaviour of the phoropter can be expressed with the following function that expresses the static behaviour relatively to a reference temperature Tref and to a related reference optical power Pref, i.e. the active lens has a Pref optical power at the Tref temperature:

$$Pcurrent = Pref + \alpha^*(Tcurrent - Tref)$$

where Pcurrent is the real/actual optical power and $\alpha$ the sensitivity to the temperature (in dioptry/° C.).

Knowing this information defining the static behaviour of the phoropter, and the measured temperature at the time of the correction, one can deduce the correction to apply to the optical power control command to bring back the actual optical power equal to the expected optical power when the phoropter is in a steady state condition during its utilization.

Now if the temperature sensor has the same specific heat than the one of the active lens, then the measured temperature is a perfect image of the one of the active lens and there is no need to add a dynamic correction.

For the dynamic behaviour, measurements of the evolutions of the temperature by the temperature sensor and of the actual optical power of the active lens are done when and after steps of temperature are applied to the phoropter and while it is not in a steady state (steady state is when its temperature is stable and its optical power is finally stable or the measurements have been done for a sufficient long time) for each step. The step of temperature can be applied externally by the controlled temperature chamber. The step of temperature can instead be applied internally by switching on or off the phoropter and measuring the evolutions of the measured temperature and of the actual optical power. Again, those measurements are done with all other controllable parameters that could modify the optical power constant and notably the optical power control command that is set to a defined value. Again, this can be repeated for other values of the other controllable parameters and typically for other values of optical power control command.

With all those measurements, it is possible to create with known mathematical tools a dynamic curve or a dynamic function of the actual optical power of the active lens as a function of the time and/or duration and/or the rate of change of temperature . . . and, for example, the dynamic behaviour of the phoropter can be expressed with the following function that expresses the dynamic behaviour relatively to a reference temperature Tref and to a related reference optical power Pref:

$$Pcurrent = Pref + \alpha^*(Tcurrent - Tref + \gamma^*(TswitchOn - TlastSwitchOff)^* e^{-(t/\delta)})$$

where Pcurrent is the actual optical power, $\alpha$ the sensitivity to the temperature, $\gamma$ a temperature coefficient, $\delta$ a coefficient related to the dynamic of the reactivity of the system, essentially related to the one of the liquid of the active lens, and TswitchOn the measured temperature when the phoropter was switched on and TlastSwitchOff the temperature when the phoropter was switched off for the last time.

Knowing this information defining the dynamic behaviour of the phoropter, and the measured temperature at the time of the correction, one can deduce the correction to apply to the optical power control command as regards the dynamic part of the shift and it is combined to the static correction to bring back the actual optical power equal to the expected optical power.

Finally, it is preferable, knowing the static and dynamic behaviour of the phoropter to define a global curve or, more easily, a global function taking into account both static and dynamic behaviours. Such a function that expresses both the static and dynamic behaviours relatively to a reference temperature Tref and to a related reference optical power Pref, i.e. the active lens has a Pref optical power at the Tref temperature, can be, for example:

$$Pcurrent = Pref + \alpha^*(Tcurrent - Tref + \beta^* e^{-(t/\delta)})$$

where Pcurrent is the real/actual optical power, $\alpha$ the sensitivity to the temperature, $\beta$ a temperature coefficient (in ° C.), $\delta$ a coefficient related to the dynamic of the reactivity of the system, essentially related to the one of the liquid of the active lens, and t the time since the change of temperature occurred or started. This formula is used for a sharp or step change of temperature such as the one occurring when switch on. It is then necessary to detect the changes of temperature and the evolution or rate of change of the temperature for a proper application of such a global function for a global correction (as for the dynamic correction by itself). For the case there is a relatively short (less than the time to reach the steady state) switch off and then a new switch on, the evolution of the optical power can be computed considering that during switch off the generated heat inside the phoropter disappears and the internal temperature decreases instead of increasing when switching on.

We have just seen a global function for correcting static and dynamic behaviour of the phoropter and that is time dependent. It is also possible to define a global function that is time dependent and dependent on the difference of temperature and in the following example, to the temperature at the switching on of the phoropter and at the switching off of the phoropter. This global function that is still defined relatively to a reference temperature Tref and to a related reference optical power Pref is:

$$Pcurrent = Pref + \alpha^*(Tcurrent - Tref + \gamma^*(TswitchOn - TlastSwitchOff)^* e^{-(t/\delta)})$$

where Pcurrent is the actual optical power, $\alpha$ the sensitivity to the temperature, $\gamma$ a temperature coefficient, $\delta$ a coefficient related to the dynamic of the reactivity of the system, essentially related to the one of the liquid of the active lens, and TswitchOn the measured temperature when the phoropter was switched on and TlastSwitchOff the temperature when the phoropter was switched off for the last time.

Even if the correction can be executed in real time and continuously, preferably, the correction is done only when a patient has to be examined in order to reduce the correction workload in the phoropter which correction workload could by itself increase the heat of the parts and electronic circuits of the phoropter.

Figure 1:
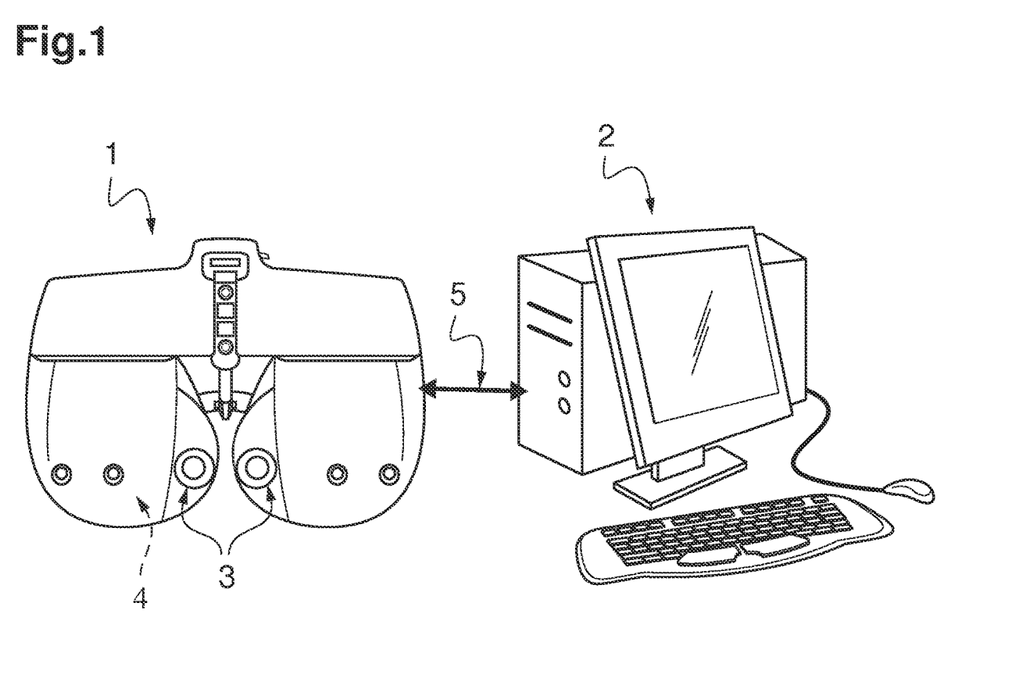
FIG. 1 is a schematic view of a phoropter and of its computing system symbolized as a microcomputer.

In FIG. 1, a phoropter 1 is shown. This phoropter is controlled by electronic circuits, practically of the programmable type with a microcontroller or microprocessor. Those programmable means are symbolized with a microcomputer 2 in FIG. 1 that is outside the phoropter but depending of the embodiments, those electronic circuits and the programmable part of them may be inside the phoropter or shared between the inside of the phoropter and an external device. The functional connections between the microcomputer 2 and the internal parts of the phoropter that are controlled or read/measured electronically are symbolized with a double end arrow 5. At least one active lens 3 in front of the patient eye, typically two, one for each eye of the patient that is examined with the phoropter, that are electronically controllable, are arranged within the phoropter. A temperature sensor 4 that is electronically readable is also arranged within the phoropter (referenced 4 with a discontinued arrow in FIG. 1 because not visible from the outside of the phoropter).

In addition to the electronic circuits inside the phoropter, other electrical parts may be found in it, for example a power supply. Those circuits and parts are generally generating some heat, and this causes an increase of the internal temperature of the phoropter and thus a shift of the optical power of the active lens that is subjected to such a temperature increase.

One can understand that variations of the temperature inside the phoropter may thus have internal origin, i.e. at switching on or off of the phoropter or even when activating some parts of the phoropter, but also have an external origin. The external origin may be caused for example by some airflow due to the opening of a door or window or to solar rays reaching the phoropter. Generally, the external origin of temperature variations is limited thanks to the fact that the phoropter is in a room that has some king of temperature control, e.g. air conditioning.

Figure 2:
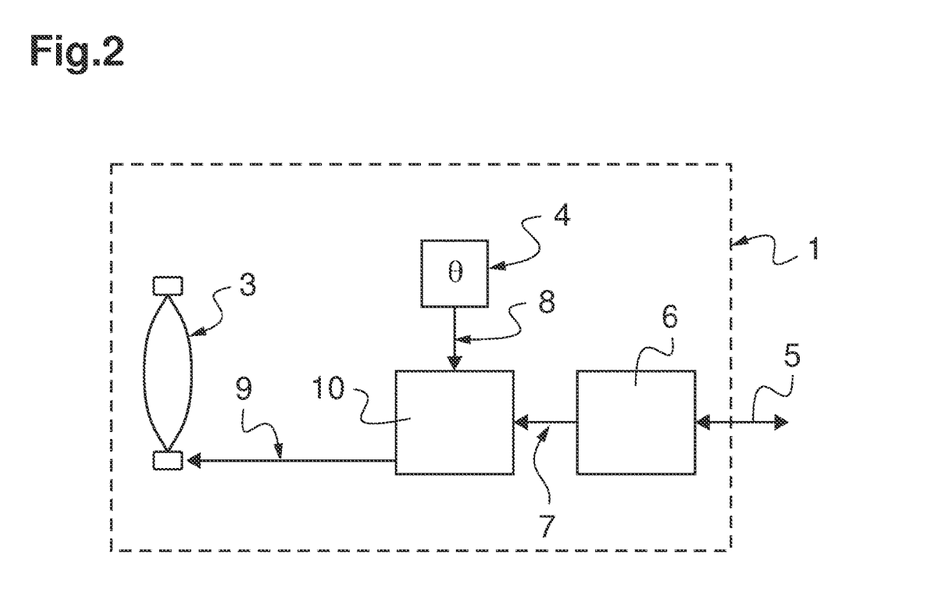
FIG. 2 is a simplified schematic view of part of the internal elements that are related to the process of the invention.

In FIG. 2, the functional relations between the active lens 3, the temperature sensor 4, and the relevant electronic circuits that allow the operation of the phoropter may be better understood. The electronic part 6 that globally controls the phoropter and provide the optical power control command 7 has been separated from the electronic part 10 that is correcting the optical power control command 7 as a function of the temperature signal 8 measured by the temperature sensor 4 for ease of explanation. One can understand that the correction may be done directly inside the electronic part that globally controls the phoropter and that also receives the temperature signal, specifically if it is done numerically in a programmable processor or it may be corrected externally in the external microcomputer 2 that then also receives the measured temperature. The active lens 3 then receives a control command or signal 9 that is corrected according to the temperature signal 8 in order to have the actual optical power of the active lens equal or close to the expected one corresponding to the optical power control command 7 intended for an expected optical power that supposed there was no temperature shift.

The invention claimed is:

1. A process of correction of a shift of an optical power of an active lens in a phoropter due to a temperature change over time, the active lens comprising a container filled with a liquid and having a deformable curvature membrane under an action of an actuator controlled by an optical power control command, the shift being that the active lens provides an actual optical power that is different from an expected optical power corresponding to the optical power control command, the process comprising:
  measuring, using a temperature sensor arranged in and/or on the phoropter, the temperature in the phoropter;
  obtaining, in a preliminary phase, a static curve or function of the actual optical power of the active lens as a function of measured temperatures for at least one constant value of optical power control command and in steady state condition;
  in a further utilization phase of the phoropter, measuring a current temperature by the temperature sensor, and receiving, by the active lens, an optical power control command that is corrected using the static curve or function of the actual optical power of the active lens to bring back the actual optical power equal to the expected optical power; and
  obtaining, in the preliminary phase, a further dynamic curve or function of the actual optical power of the active lens as a function of a time for at least one constant value of optical power control command and for at least one defined step of temperature change, the actual optical power becoming constant after a settle time as from a start of the step of temperature change, and, in the further utilization phase of the phoropter, the active lens receiving an optical power control command that is further corrected using the dynamic curve or function of the actual optical power of the active lens to bring back the actual optical power equal to the expected optical power.

2. The process according to claim 1, wherein the phoropter is configured to be switched on or off and comprises electronic and electric or mobile mechanical parts, that warm up when the phoropter is switched on, and wherein during the preliminary phase for obtaining the further dynamic curve or function of the actual optical power of the active lens as a function of the time, the defined step of temperature change is only obtained by switching on or off the phoropter.

3. The process according to claim 1, wherein in the further utilization phase of the phoropter, the active lens receives an optical power control command that is further corrected using the dynamic curve or function of the actual optical power of the active lens as a function of a time to bring back the actual optical power equal to the expected optical power, a value of the correction being dependent of a time since switching on of the phoropter.

4. The process according to claim 3, wherein in the further utilization phase of the phoropter, a global function corresponding to the combination of the static and dynamic curves or functions of the actual optical power of the active lens is used for the correction.

5. The process according to claim 4, wherein in the further utilization phase of the phoropter, the global function is defined relatively to a reference temperature Tref and to a related reference optical power Pref:

$$P\text{current} = P\text{ref} + \alpha^*(T\text{current} - T\text{ref}) + \gamma^*(T\text{switchOn} - T\text{lastSwitchOff})^* e^{-(t/\delta)}$$

where Pcurrent is the actual optical power, α a sensitivity to the temperature, γ a temperature coefficient, δ a coefficient related to a dynamic of reactivity of a system, essentially related to the one of the liquids of the active lens, and TswitchOn the measured temperature when the phoropter was switched on and Tlast- SwitchOff the temperature when the phoropter was switched off for the last time.

6. The process according to claim 1, wherein in the further utilization phase of the phoropter, a global function corresponding to the combination of the static and dynamic curves or functions of the actual optical power of the active lens is used for the correction.

7. The process according to claim 6, wherein in the further utilization phase of the phoropter, the global function is defined relatively to a reference temperature Tref and to a related reference optical power Pref:

$$P\text{current}=P\text{ref}+\alpha*(T\text{current}-T\text{ref}+\beta*e^{-(t/\delta)})$$

where Pcurrent is the actual optical power, α a sensitivity to the temperature, β a temperature coefficient, δ a coefficient related to a dynamic of reactivity of a system, essentially related to the one of the liquids of the active lens, and t the time since the change of temperature occurred or started.

8. An optometry system comprising:
a phoropter comprising at least one active lens, the active lens comprising a container filled with a liquid and having a deformable curvature membrane under an action of an actuator controlled by an optical power control command; and
processing circuitry configured to
  measure, using a temperature sensor arranged in and/or on the phoropter, temperature in the phoropter,
  obtain, in a preliminary phase, a static curve or function of the actual optical power of the active lens as a function of measured temperatures for at least one constant value of optical power control command and in steady state condition,
  measure, in a further utilization phase of the phoropter, a current temperature by the temperature sensor, the active lens receiving an optical power control command that is corrected using the static curve or function of the actual optical power of the active lens to bring back the actual optical power equal to an expected optical power, and
  obtain, in the preliminary phase, a further dynamic curve or function of the actual optical power of the active lens as a function of a time for at least one constant value of optical power control command and for at least one defined step of temperature change, the actual optical power becoming constant after a settle time as from a start of the step of temperature change, and, in the further utilization phase of the phoropter, the active lens receiving an optical power control command that is further corrected using the dynamic curve or function of the actual optical power of the active lens to bring back the actual optical power equal to the expected optical power.

9. The optometry system according to claim 8,
wherein in the further utilization phase of the phoropter, a global function corresponding to the combination of the static and dynamic curves or functions of the actual optical power of the active lens is used for the correction, and
wherein in the further utilization phase of the phoropter, the global function is defined relatively to a reference temperature Tref and to a related reference optical power Pref:

$$P\text{current}=P\text{ref}+\alpha*(T\text{current}-T\text{ref}+\beta*e^{-(t/\delta)})$$

where Pcurrent is the actual optical power, α a sensitivity to the temperature, β a temperature coefficient, δ a coefficient related to a dynamic of reactivity of a system, essentially related to the one of the liquids of the active lens, and t the time since the change of temperature occurred or started.

10. The optometry system according to claim 8
wherein in the further utilization phase of the phoropter, a global function corresponding to the combination of the static and dynamic curves or functions of the actual optical power of the active lens is used for the correction, and
wherein in the further utilization phase of the phoropter, the global function is defined relatively to a reference temperature Tref and to a related reference optical power Pref:

$$P\text{current}=P\text{ref}+\alpha*(T\text{current}-T\text{ref}+\gamma*(T\text{switchOn}-T\text{lastSwitchOff})*e^{-(t/\delta)})$$

where Pcurrent is the actual optical power, α a sensitivity to the temperature, γ a temperature coefficient, δ a coefficient related to a dynamic of reactivity of a system, essentially related to the one of the liquids of the active lens, and TswitchOn the measured temperature when the phoropter was switched on and TlastSwitchOff the temperature when the phoropter was switched off for the last time.

\* \* \* \* \*